United States Patent
Spitz et al.

(10) Patent No.: US 7,018,391 B2
(45) Date of Patent: Mar. 28, 2006

(54) METHODS AND APPARATUS FOR REMOVING VEINS

(75) Inventors: Gregory A. Spitz, Batavia, IL (US); Douglas D. Sjostrom, Tewksbury, MA (US); Alexander D Grinberg, Newton, MA (US); Michael A. Long, Somerville, MA (US)

(73) Assignee: Smith & Nephew North America, DE (US)

( * ) Notice: Subject to any disclaimer, the term of this patent is extended or adjusted under 35 U.S.C. 154(b) by 636 days.

(21) Appl. No.: 10/059,148

(22) Filed: Jan. 31, 2002

(65) Prior Publication Data

US 2002/0082632 A1 Jun. 27, 2002

Related U.S. Application Data

(63) Continuation of application No. 09/444,925, filed on Nov. 24, 1999, now Pat. No. 6,436,116, which is a continuation-in-part of application No. 09/289,172, filed on Apr. 9, 1999, now abandoned, which is a continuation of application No. 08/944,384, filed on Oct. 6, 1997, now Pat. No. 5,893,858.

(51) Int. Cl.
*A61B 17/00* (2006.01)

(52) U.S. Cl. .......................... 606/190; 604/21

(58) Field of Classification Search ................ 600/156, 600/160, 476, 478; 604/20, 21; 607/88, 607/92; 606/190
See application file for complete search history.

(56) References Cited

U.S. PATENT DOCUMENTS 3,590,232 A 6/1971 Sadowski
3,945,375 A 3/1976 Banko
4,126,136 A 11/1978 Auth et al.
4,249,533 A 2/1981 Komiya
4,311,138 A 1/1982 Sugarman
4,313,431 A 2/1982 Frank
4,499,899 A 2/1985 Lyons, III
4,562,838 A 1/1986 Walker
4,693,244 A 9/1987 Daikuzono
4,793,346 A 12/1988 Mindich
4,811,734 A 3/1989 McGurk-Burleson et al.
4,850,354 A 7/1989 McGurk-Burleson et al.

(Continued)

FOREIGN PATENT DOCUMENTS

DE 36 03 782 10/1987

(Continued)

OTHER PUBLICATIONS

R. A. Weiss. MD, "Transillumination Mapping Prior To Ambulatory Phlebectomy", Apr. 30, 1999, vol. 12, p. 3-6.

(Continued)

*Primary Examiner*—David O. Reip
(74) *Attorney, Agent, or Firm*—Fish & Richardson P.C.

(57) ABSTRACT

A method for removing a vein includes making an incision through a skin layer of a patient, inserting a surgical instrument through the incision, visualizing the vein through the skin layer using a light source positioned subcutaneously and in proximity of the vein, and cutting the vein using the surgical instrument. The vein can be visualized by directing light from the light source at the vein from underneath the vein or from a side of the vein. A device for illuminating a body structure has a housing with a distal end configured for subcutaneous insertion into a patient's tissue and positioning in proximity of the body structure, a light path supported by the housing and configured for directing light at the body structure, and a fluid line supported by the housing.

10 Claims, 8 Drawing Sheets

U.S. PATENT DOCUMENTS

| | | | |
|---|---|---|---|
| 4,867,157 | A | 9/1989 | McGurk-Burleson et al. |
| 4,895,145 | A | 1/1990 | Joffe et al. |
| 4,896,015 | A | 1/1990 | Taboada et al. |
| 4,944,738 | A | 7/1990 | Rodriguez |
| 4,976,710 | A | 12/1990 | Mackin |
| 5,011,483 | A | 4/1991 | Sleister |
| 5,029,573 | A | 7/1991 | Chow ............... 128/4 |
| 5,061,266 | A | 10/1991 | Hakky |
| 5,084,043 | A | 1/1992 | Hertzmann |
| 5,084,052 | A | 1/1992 | Jacobs |
| 5,085,657 | A | 2/1992 | Ben-Simhon |
| 5,102,410 | A | 4/1992 | Dressel |
| 5,147,354 | A | 9/1992 | Boutacoff et al. |
| 5,156,604 | A | 10/1992 | Huessel et al. |
| 5,188,634 | A | 2/1993 | Hussein et al. |
| 5,203,353 | A | 4/1993 | Easley et al. |
| 5,224,944 | A | 7/1993 | Elliott |
| 5,254,115 | A | 10/1993 | Bhatta et al. |
| 5,257,989 | A | 11/1993 | Celaya et al. |
| RE34,556 | E | 3/1994 | Sjostrom et al. |
| 5,312,399 | A | 5/1994 | Hakky et al. |
| 5,313,962 | A | 5/1994 | Obenchain |
| 5,320,617 | A | 6/1994 | Leach |
| 5,342,358 | A | 8/1994 | Daikuzono |
| 5,373,840 | A | 12/1994 | Knighton |
| 5,409,483 | A | 4/1995 | Campbell et al. |
| 5,447,493 | A | 9/1995 | Blugerman et al. |
| 5,531,739 | A | 7/1996 | Trelles |
| 5,571,098 | A | 11/1996 | Domankevitz et al. |
| 5,588,952 | A | 12/1996 | Dandolu |
| 5,611,357 | A | 3/1997 | Suval |
| 5,611,358 | A | 3/1997 | Suval |
| 5,665,101 | A | 9/1997 | Becker et al. |
| 5,667,480 | A | 9/1997 | Knight et al. |
| 5,782,795 | A | 7/1998 | Bays |
| 5,792,168 | A | 8/1998 | Suval |
| 5,810,806 | A | 9/1998 | Ritchart et al. |
| 5,893,858 | A | 4/1999 | Spitz |
| 5,902,315 | A | 5/1999 | DuBois |
| 5,913,857 | A | 6/1999 | Ritchart et al. |
| 5,922,004 | A | 7/1999 | DuBois |
| 6,013,073 | A | 1/2000 | Choukroun |
| 6,129,661 | A | 10/2000 | Iafrati et al. |
| 6,193,653 | B1 | 2/2001 | Evans et al. |
| 6,206,823 | B1 | 3/2001 | Kolata et al. |

FOREIGN PATENT DOCUMENTS

| | | |
|---|---|---|
| WO | WO 89/07913 | 9/1989 |

OTHER PUBLICATIONS

"Endoscopically Guided Percutaneous Diskectomy", Coherent Brochure.

James C.Y. Chow, M.D. "Endoscopic Release of the Carpal Ligament: A New Technique for Carpal Tunnel Syndrome," *Anthroscopy: The Journal of Anthroscopic and Related Surgery* 5(1): 19-24 (1989).

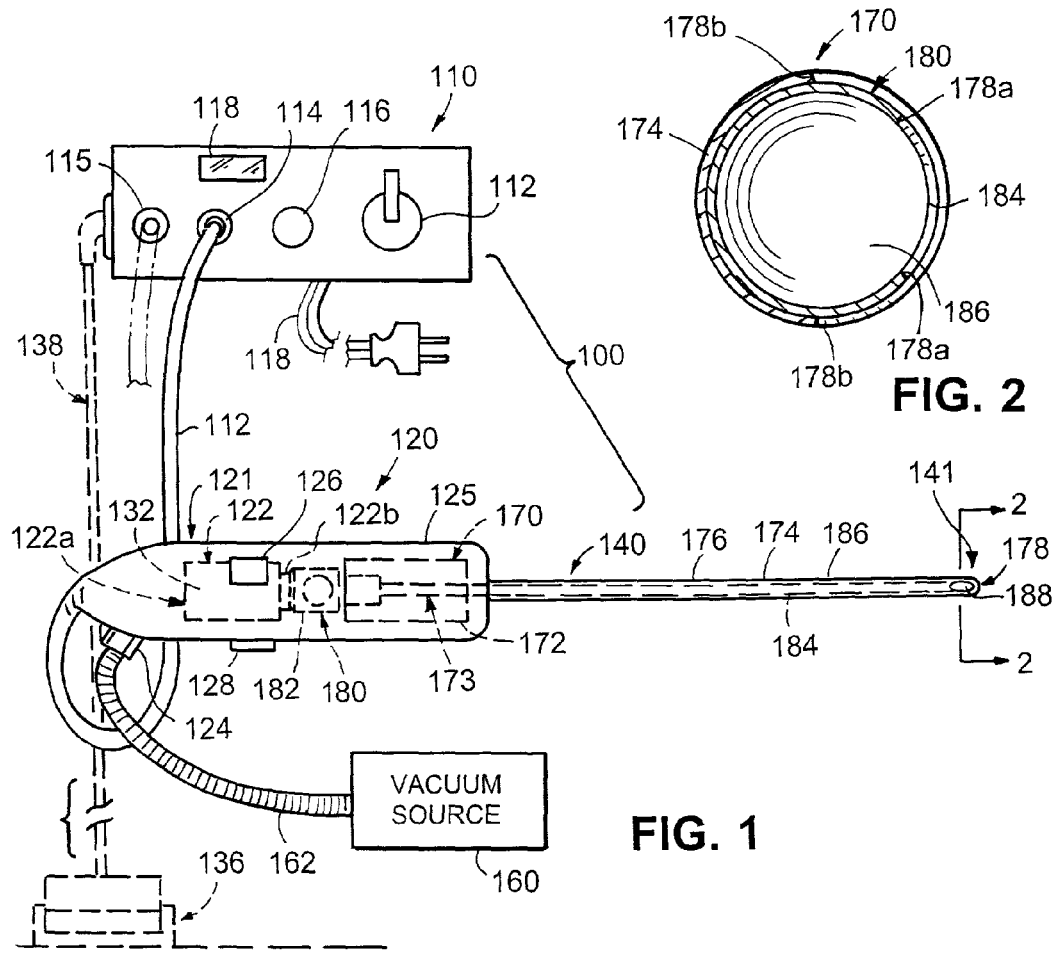
FIG. 2
FIG. 1
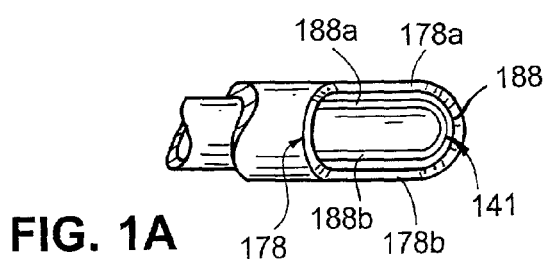
FIG. 1A

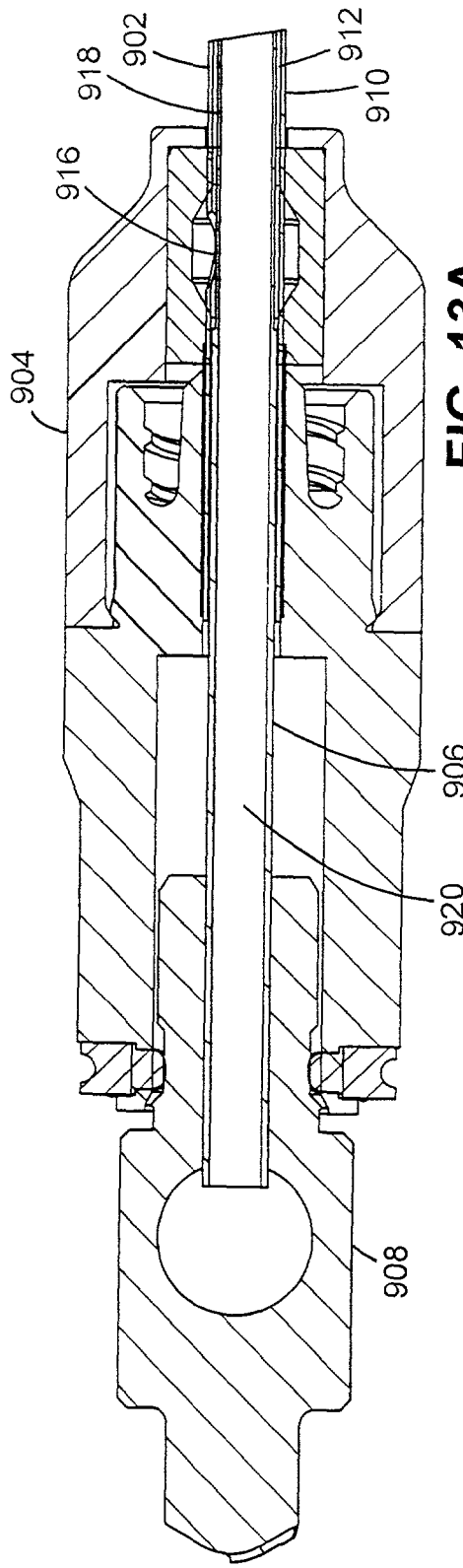
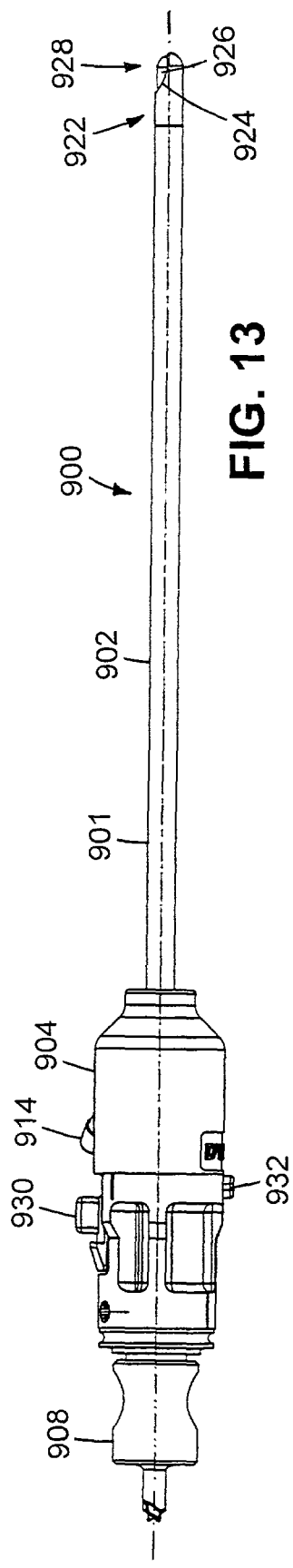
FIG. 13A
FIG. 13

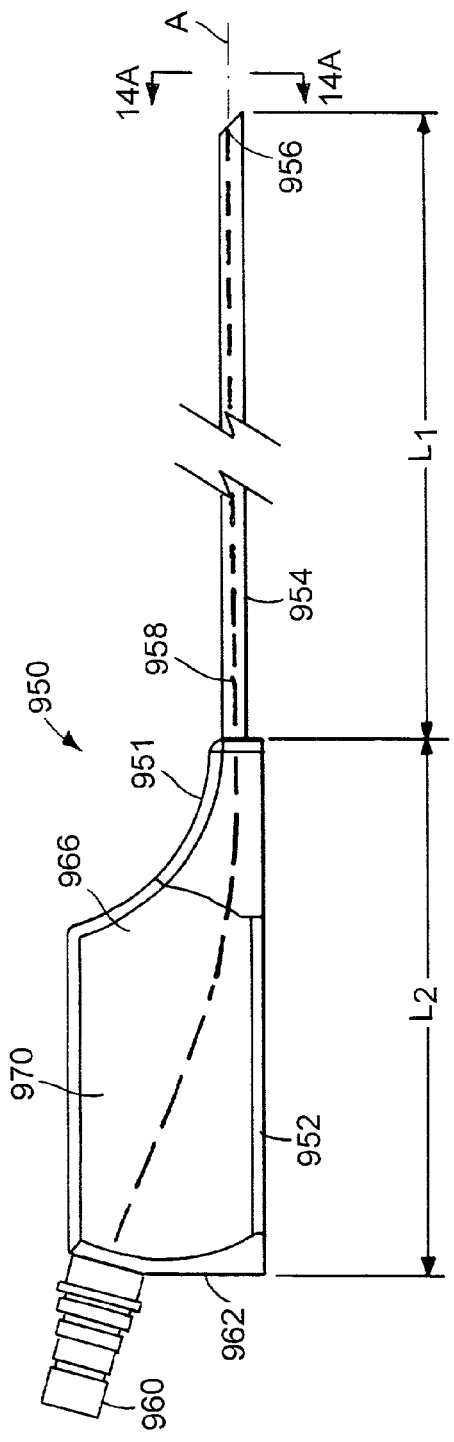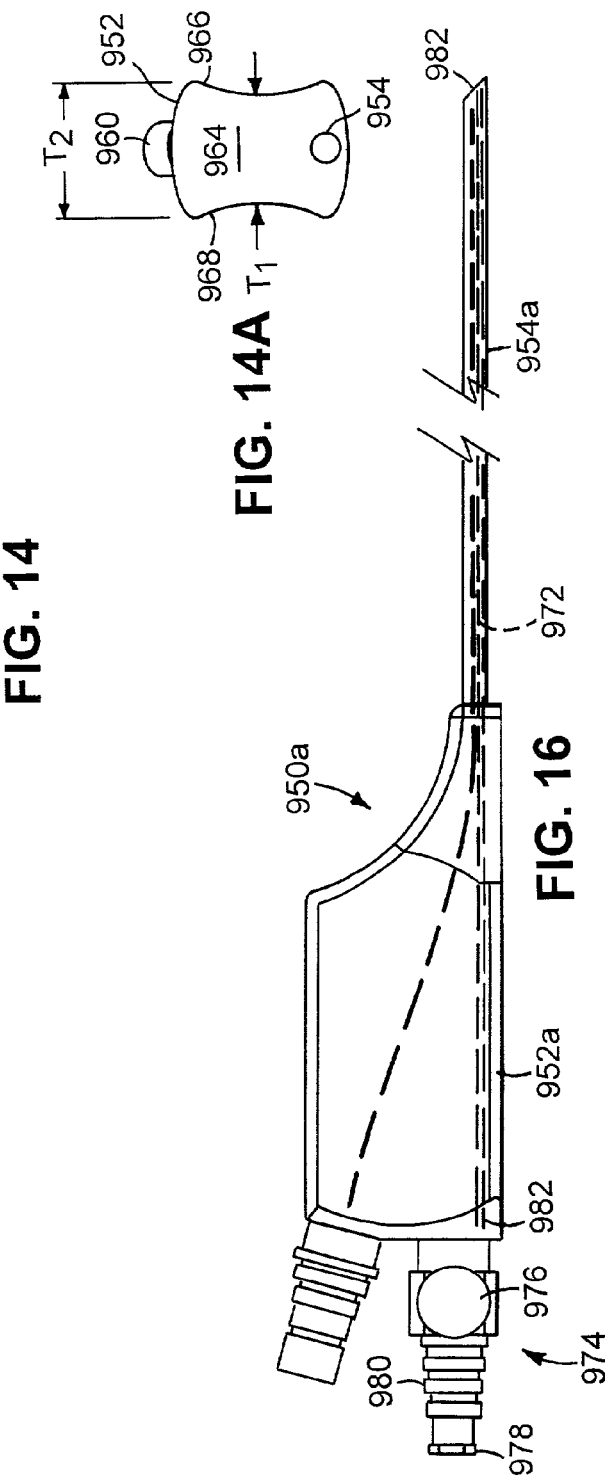

METHODS AND APPARATUS FOR REMOVING VEINS

CROSS REFERENCE TO RELATED APPLICATIONS

This application is a continuation of U.S. application Ser. No. 09/444,925,entitled METHODS AND APPARATUS FOR REMOVING VEINS, filed Nov. 24, 1999, issued as U.S. Pat. No. 6,436,116, which is a continuation-in-part of application U.S. Ser. No. 09/289,172, entitled METHODS AND APPARATUS FOR REMOVING VEINS, filed Apr. 9, 1999, now abandoned, which is a continuation of application U.S. Ser. No. 08/944,384, entitled METHODS AND APPARATUS FOR REMOVING VEINS, filed Oct. 6, 1997, issued as U.S. Pat. No. 5,893,858.

FIELD OF THE INVENTION

The present invention relates generally to surgical apparatus and procedures. More particularly, it relates to methods and apparatus for removing veins, such as, varicose veins and spider veins, in a venous system of a patient.

BACKGROUND OF THE INVENTION

Ten to fifteen percent of the population is plagued with varicose veins and spider veins. These veins have usually lost their ability to carry blood back to the heart and blood often accumulates in these veins. As a result, the veins may become swollen, distorted, and prominent. This condition is usually caused by inefficient or defective one-way valves which prevent blood from draining back through the vein.

A number of factors can contribute to the development of varicose veins and spider veins, including heredity, obesity, posture, standing or sitting for long periods of time, hormonal shifts, and excessive heat. Varicose veins may cause patients to experience various symptoms, such as, for example, aching, burning, swelling, cramping, and itching, while more serious complications of varicose veins can include thrombophlebitis, dermatitis, hemorrhage and ulcers. If these varicose veins are not treated, blood clots may form in the vein, and phlebitis or inflammation of the inside lining of the vein may occur. Even absent such symptoms, many patients seek medical treatment of varicose or spider veins for cosmetic reasons.

Various approaches have been developed to treat varicose veins. In less complicated cases, elevation of the legs and use of support hosiery may be sufficient therapy to stop or slow the progression of the varicose veins. Alternatively, a technique called "sclerotherapy" may be used to treat varicose veins. In this procedure, the affected veins are injected with a sclerosing solution, such as sodium tetradecyl sulfate or pilocainol. Approximately one injection of the solution is usually administered for every inch of the affected veins, and multiple injections may be administered during a treatment session. The sclerosing solution causes subsequent inflammation and sclerosis of the veins. The sclerosis results in localized scarring or closure of the veins, which forces rerouting of the blood away from the affected veins.

However, patients usually have to undergo two or more sclerotherapy treatments in order to alleviate the varicose and spider veins to a satisfactory degree. Other fine reddish blood vessels may also appear around the treated area, requiring further injections. Nevertheless, the sclerotherapy technique may not be a permanent or complete solution since the condition of the varicose and spider veins may reoccur within five years.

Sclerotherapy also has other potential complications, including browning splotches or bruising of the skin, formation of blood clots in the veins, inflammation, adverse allergic reactions, ulceration, phlebitis, anaphylactic overdose, ischemia, skin or fat necrosis, and peripheral neuropathy. Furthermore, sclerotherapy cannot be applied to the saphenous vein in the upper thigh region due to the risk of sclerosis of the deep veins. Thus, the sclerotherapy technique is often combined with an operative procedure, such as ligation of a portion of the saphenous vein.

Another technique to treat varicose veins is called stabavulsion phlebectomy with hooks. In this technique, one or more incisions are made in the skin of the patient, and a hook is inserted into the incision to grip or hook the veins to be removed. When the veins are grabbed, the veins are pulled through the surgical incision and severed. However, this procedure usually requires two surgeons to perform the procedure and takes about 2–3 hours. In addition, this procedure usually requires multiple incisions in the patient in order to hook the affected veins. Furthermore, it is often difficult to completely remove the entire affected veins using this procedure.

Varicose veins can also be removed by a procedure commonly referred to as "stripping." To remove a saphenous vein using this stripping procedure, a large incision is made near the groin area of a patient and the saphenous vein is separated from the femoral vein. The saphenous vein is also usually dissected near the lower portion of the leg. Multiple large incisions are made along the leg in order to sever and ligate the tributary veins of the saphenous vein. A vein stripper, such as a wire, is then inserted into the lumen of the saphenous vein. The wire is then inserted through the saphenous vein to the groin incision and tied to the lower end of the vein. The wire is then removed through the groin incision to extract the vein. After the saphenous vein is completely removed from the leg, the large incisions along the leg are closed.

However, the stripping procedure is usually painful and often requires overnight hospitalization. In addition, numerous incisions are usually required to remove the saphenous vein and its branches which often leave permanent unsightly scars along the leg of a patient. Additionally, the large incisions create a risk of infection to the patient and may not heal properly, especially patients who have poor circulation in their extremities. There are also associated complications with this technique, such as, for example, blood loss, pain, infection, hematoma, nerve injury, and swelling.

SUMMARY OF THE INVENTION

In view of the above, the present invention provides methods and apparatus for removing undesired veins, such as, varicose and spider veins, in a venous system of a patient. The apparatus and methods of the present invention provide an efficient and minimally intrusive procedure to remove the undesired veins. The undesired veins can be completely removed with minimal scarring and without hospitalization. The methods and apparatus can also reduce operating time in the removal of the undesired veins, and the entire procedure can be performed by a single surgeon in less time than traditional procedures.

According to one aspect of the invention, a method for removing a vein includes making an incision through a skin layer of a patient, inserting a surgical instrument through the incision, visualizing the vein through the skin layer using a light source positioned subcutaneously and in proximity of the vein, and cutting the vein using the surgical instrument.

Embodiments of this aspect of the invention may include one or more of the following features.

Visualizing the vein includes directing light from the light source at the vein from underneath the vein or from a side of the vein.

In one illustrated embodiment, the surgical instrument is provided with the light source. The light source is a fiberoptic, e.g., a fiberoptic bundle.

The method further includes irrigating and tumescing a surgical region in proximity to the vein using the surgical instrument, and aspirating cut veinous tissue through the surgical instrument.

In another embodiment, visualizing the vein includes providing a second instrument including the light source, making a second incision through a skin layer of the patient, and inserting the second instrument through the incision. A surgical region in proximity to the vein is irrigated and tumesced using the second instrument.

According to another aspect of the invention, a method of visualizing a body structure includes positioning an illuminating device subcutaneously such that light is directed at the body structure, and observing the body structure through a skin layer of the patient overlying the body structure.

Embodiments of this aspect of the invention may include one or more of the following features.

Visualizing the body structure includes directing light from the illuminating device at the body structure from underneath the body structure or from a side of the body structure.

According to another aspect of the invention, a device for illuminating a body structure has a housing with a distal end configured for subcutaneous insertion into a patient's tissue and positioning in proximity of the body structure, a light path supported by the housing and configured for directing light at the body structure, and a fluid line supported by the housing.

Embodiments of this aspect of the invention may include one or more of the following features.

The housing includes a connector for connecting the light path to a light transmitter. The connector extends from a proximal end of the housing substantially in the direction of a longitudinal axis of the housing. The housing has a generally hour glassed-shape handle in cross-section. The light path is a fiberoptic, e.g., a fiberoptic bundle.

According to another aspect of the invention, a device for cutting tissue includes a surgical instrument with a distal end configured for subcutaneous insertion into a patient's tissue and positioning in proximity of the tissue. The surgical instrument includes an outer tube defining a lumen, and an inner tube located within the outer tube. The inner tube has a cutter and is movable relative to the outer tube to cut tissue. A light path is supported by the surgical instrument and is configured for directing light at a region adjacent the cutter and at a skin layer overlying the tissue.

Embodiments of this aspect of the invention may include one or more of the following features.

A fluid line is supported by the surgical instrument. The inner tube defines an aspiration path, and the inner tube and outer tube define a fluid path therebetween. The inner tube is configured to rotate at a speed of about 500–2000 rpm.

Among other advantages, the illuminating device of the invention can provide the surgeon with a subcutaneous light source that has more fibers, is of smaller size, is less traumatic, and has superior ergonomics to presently available surgical light sources such as endoscopes. Furthermore, as compared to an endoscope, if the illuminating device of the invention is bent during use, there are no expensive optics that can be damaged.

The invention, together with further attendant advantages, will best be understood by reference to the following detailed description of the presently preferred embodiments of the invention, taken in conjunction with the accompanying drawings. It is to be understood that both the foregoing general description and the foregoing detailed description are exemplary and explanatory and are intended to provide further explanation of the invention as claimed.

BRIEF DESCRIPTION OF THE DRAWINGS

FIG. 1 is a side elevational view of a surgical system to remove undesired veins in a venous system of a patient;

FIG. 1A is a fragmentary side view of the distal end of a surgical instrument of the surgical system of FIG. 1;

FIG. 2 is a cross-sectional view taken about line 2—2 of FIG. 1;

FIG. 13 shows an additional embodiment of a surgical instrument for removing undesired veins;

FIG. 13A is a cross-sectional view of a proximal end of the surgical instrument of FIG. 13;

FIG. 14 illustrates a fiberoptic transilluminator;

FIG. 14A is an end view of the fiberoptic transilluminator of FIG. 14, taken along lines 14A—14A;

FIG. 16 illustrates an additional embodiment of a fiberoptic transilluminator;

DESCRIPTION OF THE PREFERRED EMBODIMENTS

Figure 3:
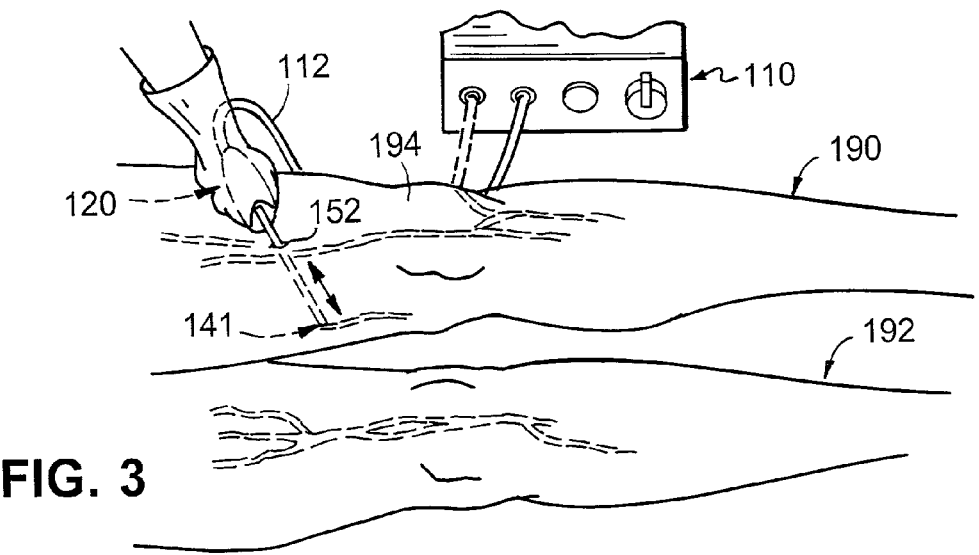
FIG. 3 is a diagrammatical view of undesired veins being removed from the legs of a patient by the surgical system of FIG. 1.

Before explaining the preferred embodiments in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the preferred embodiments of the present invention for the convenience of the reader and are not for the purpose of limitation.

Referring now to the drawings in detail, and particularly to FIG. 1, a preferred embodiment of a surgical system 100 to remove undesired veins in a venous system of a patient is illustrated. The surgical system 100 allows a single surgeon to remove veins from a patient more quickly than traditional techniques. The undesired veins can be completely removed with minimal scarring and without hospitalization. The surgical system 100 can also allow two or more surgeons to remove undesired veins of a patient at the same time.

As shown in FIG. 1, the surgical system 100 generally includes a control unit 110 and a surgical instrument 120. The control unit 110 sends electrical signals through a cable 112 at a selected amplitude and frequency. The electrical signals energize a motor 122 of the surgical instrument 120 which drives a cutting element 141 at a selected speed. The speed of the cutting element 141 of the surgical instrument 120 is controlled and monitored by the control unit 110.

The surgical instrument 120 of the surgical system 100 can be utilized by a surgeon to remove undesired veins in a leg 190 of a patient. A second handpiece assembly (not shown) may also be connected to the control unit 110 to allow a second surgeon to remove undesired veins in the other leg 192 or another portion of the patient. It will be recognized that any suitable number of surgical instrument 120 can be attached to the control unit 110 to remove undesired veins.

Figure 5:
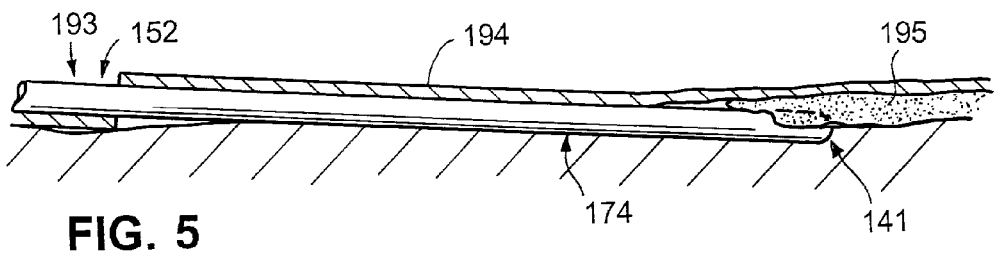
FIG. 5 is a cross-sectional view taken about line 5—5 of FIG. 4.

As illustrated in FIG. 3, one or more small incisions 152 (one being shown) are made through the skin layer 194 of the patient near the undesired veins. The distal end of the surgical instrument 120 is inserted through the small incision 152. Once the distal end of the surgical instrument 120 is inserted through the incision 152, the cutting element 141 is energized at a desired speed. The cutting element 141 is then placed in contact with an undesired vein 195 of the patient as shown in FIG. 3 and 5. The portion of the vein 195 that contacts the cutting element 141 is cut up into small or tiny particles or pieces.

The particles of the undesired vein 19S are removed from the surgical site to a suction or vacuum source 160. After the particles are removed, the small incision 152 can be closed with steri-strips or any suitable closure material. Although these incisions can be closed with sutures, it is considered unnecessary due to the small size of the incisions, and is also undesirable since suturing the skin can cause scarring.

Referring again to FIG. 1, the control unit 110 of the surgical system 100 preferably includes a control system (not shown) integral to the control unit 110, an on-off switch 112, jacks or connectors 114 and 115, a power control switch 116, and a display 118. The control unit 110 sends signals to the surgical instrument 120 to control the acceleration, deceleration, and speed of the cutting element 141 of the surgical instrument 120. The control unit 110 may also monitor the speed of the cutting element 141 in order to limit the speed and the torque of the cutting element 141 to within preselected limits for optimum performance of the surgical instrument 120 being used. It will be recognized that the control unit 110 may drive the cutting element 141 at any suitable speed and torque.

The on-off switch 112 of the surgical system 100 controls the electrical power to the control unit 110 to allow the surgeon to actuate the cutting element 141 of the surgical instrument 120. When the on-off switch 112 is activated, the control unit 110 provides power to drive the cutting element 141 of the surgical instrument 120 at a desired speed.

The jack 114 of the control system 110 is attached to the proximal end of the cable 112 to allow the surgical instrument 120 to be connected to the control unit 110. The jack 115 of the control system provides another connector to allow another cable of a surgical instrument to be coupled to the control unit 110. Although only two jacks 114 and 115 are shown, it is contemplated that any suitable number of jacks may be incorporated into the control unit 110.

The control unit 110 also has a power line 118 for insertion in an electro-signal unit or conventional outlet. It is contemplated that the control unit 110 may also be powered by a direct current (DC) source, such as a battery. The control unit 110 may be any suitable control unit, such as Model No. PS3500EP™ or Dyonics®EP-1 surgical drive system available from Smith & Nephew.

Referring still to FIG. 1, the surgical instrument 120 generally includes a motor drive unit or handpiece assembly 121 and a blade assembly 140. The handpiece assembly 121 includes a motor 122, a suction nozzle 124, a housing or an outer casing 125, a trigger mechanism 126, and a vacuum switch 128. The distal end of the handpiece assembly 121 is sized and configured to receive the blade assembly 140, and proximal end of the handpiece assembly 121 is coupled to the control unit 110 by the cable 112. The cable 112 may include ducts or vents to allow air or a cooling fluid to be introduced into the handpiece assembly 121 to cool the motor 122. A suitable handpiece assembly 121 may be Model Nos. 7205354, 72-5355, or 72-5357, available from Smith & Nephew.

The housing 125 of the handpiece assembly 121 is adapted to isolate the operator from the inner components of the handpiece assembly 121. The housing 125 is preferably substantially cylindrically shaped and is adapted to be held by a user in a conventional manner, but may be any suitable shape or size which allows it to be grasped by the user. While a single or unitary component housing 125 is illustrated, the housing 125 may comprise multiple parts or pieces.

The housing 125 of the handpiece assembly 121 can be constructed from a plastic, titanium, aluminum, or steel. It is also contemplated that the housing 125 may be made from a variety of materials including other plastics (i.e., liquid crystal polymer (LCP), nylon, or polycarbonate) or any other suitable material.

The triggering mechanism 126 of the handpiece assembly 121 allows a surgeon to activate the control unit 110 so that power may be continuously supplied to the motor 122 of the handpiece assembly 121. The triggering mechanism 126 preferably includes a switch incorporated in the handpiece assembly 121. It will be recognized that the triggering mechanism 126 may alternatively include a foot activating switch 136 that is detachably coupled or attached to the control unit 110 by a cable or cord 138.

The suction nozzle 124 of the handpiece assembly 121 is coupled to a vacuum source 160 by a hose 162. When the vacuum source 160 is activated, the source 160 draws a vacuum through a conduit (not shown) defined through the handpiece assembly 121 and the surgical instrument 120.

The vacuum source 160 causes vein tissue and other fluids to be drawn from the surgical site through the conduit of the blade assembly 140 and handpiece assembly 121 into the vacuum source 160. The vacuum source 160 can be any suitable vacuum or suction source to remove vein tissue from the surgical site. It is also contemplated that the vacuum source 160 can be a separate tool, such as, for example, a cannula, or any other suitable instrument that can be inserted in the incision to remove vein tissue.

The motor 122 of the handpiece assembly 121 is preferably disposed within the handpiece assembly 121. The motor 122 receives power from the control unit 110 over wires (not shown) in cable 112. The motor 122 preferably includes a housing 122a and a drive shaft 122b. When the motor 122 is activated, the drive shaft 122b rotates to drive the cutting element 141 of the surgical instrument 120 at a desired speed. The motor 122 is preferably a reversible rotational drive motor that can turn the drive shaft 122b in either direction or oscillate the shaft 122b back and forth. It will be recognized that the motor 122 can be any suitable device that can drive or actuate the cutting element 141 of the surgical instrument 120.

The blade assembly 140 of the surgical instrument 120 preferably includes an outer stationary member 170 and a rotatable member 180. The blade assembly 140 is preferably a disposable unit to eliminate resterilization of the portions of the assembly that enters into the patient's body. Therefore, the blade assembly 140 is removed from the handpiece assembly 121 after use and disposed of. The blade assembly 140 may include any suitable blade from the EP-1 family from Smith & Nephew, such as, for example, the full radius 3.5 mm blade (Ref. No. 7295305), or any suitable blade from Xomed® Endoscopy Products.

The distal end of the outer stationary member 170 is sized for insertion into an incision of the body via a puncture opening made through the skin. The outer stationary member 170 includes a fitting 172 and an elongated member 174. It is contemplated that the distal end of the blade assembly 140 may be bendable or may be articulable in various directions.

The fitting 172 of the outer stationary member 170 is preferably adapted to be threaded or snapped into the distal end of the handpiece assembly 121. The fitting 172 is preferably constructed from a plastic material and has an aperture 173 extending therethrough. It is contemplated that the fitting 172 may be fabricated from any suitable material. The distal end of the fitting 174 is coupled or attached to the proximal end of the elongated member 174 of the outer stationary member 170.

The elongated member 174 of the outer stationary member 170 preferably includes an aperture 176 extending longitudinally therethrough and one or more ports or openings 178 (one being shown). The elongated member 174 preferably has a length of about 5 inches and is fabricated from stainless steel. It is contemplated that the elongated member 174 may have any suitable length and can be manufactured from any suitable material.

The port 178 of the elongated member 174 is preferably located at or near the distal end of the elongated member 174. As shown in FIGS. 1A and 2, the port 178 has a generally cylindrical shape and preferably includes a pair of cutting edges 178a and 178b. The port 178 allows vein tissue to enter into the aperture 176 so that the cutting element 141 of the surgical instrument 120 can sever the tissue as further described below. It will be recognized that the port 178 can be any size and shape to receive vein tissue. It is also contemplated that a guard (not shown) may also be disposed across the port 178 to limit the amount of extraneous tissue that can enter into the port 178 to be severed.

The aperture 176 of the elongated member 174 and the aperture 173 of the fitting 172 are adapted to receive the rotatable member 180. The rotatable member 180 preferably includes a base 182 and an elongated member 184. The base 182 is preferably fabricated from plastic. It will be recognized that the base 182 may be fabricated from any suitable material. The inner rotatable member 180 is preferably rotated at various speeds by the motor 122.

The distal end of the base 182 of the rotatable member 180 is coupled to the proximal end of the elongated member 184, and the proximal end of the base 182 is coupled to the drive shaft 122b of the motor 122. When the drive shaft 122b of the motor 122 is energized, the drive shaft 122b rotates the base 182 and the elongated member 184 of the rotatable member 180 at a desired speed.

The elongated member 184 of the rotatable member 180 preferably includes an aperture 186 extending longitudinally therethrough and a cutting element 141. The elongated member 184 is preferably disposed coaxially within the elongated member 174 of the outer stationary member 172. The elongated member 184 is preferably fabricated from stainless steel. It is contemplated that the elongated member 184 may be constructed from any suitable material.

The cutting element 141 of the elongated member 184 is disposed at or near the distal end of the elongated member 184. Vein tissue that is exposed to the cutting element 141 through the port 178 of the outer stationary member 170 is cut by the cutting element 141 into small pieces. The pieces are drawn through the aperture 186 of the rotatable member 180 and through the suction nozzle 124 of the handpiece assembly 121 by the use of suction applied by the vacuum source 160.

The cutting element 141 of the rotatable member 180 preferably includes one or more ports or openings 188 (one being shown) disposed in the outer surface of the elongated member 184. The port 188 has a generally cylindrical shape and preferably includes a pair of cutting edges 188a and 188b. The cutting edges 188a and 188b of the port 188 of the rotatable member 180 are sharp and cooperate with sharpened edges 178a and 178b of the port 178 of the outer stationary member 170. The cutting element 141 may also comprise a blade, abrading burr, or ultrasonic element.

The cutting edges 188a and 188b of the port 188 are configured for cutting vein tissue when the rotatable member 180 is rotated in either direction of rotation, as selected by the surgeon. As the rotatable member 180 rotates, the port 188 of the rotatable member 180 periodically aligns with the port 178 of the outer stationary member 170 to admit vein tissue. When the vein tissue enters into the ports 178 and 188, the vein tissue is severed or sheared between the cutting edges 188a and 188b of the rotatable member 180 and the cutting edges 178a and 178b of the outer stationary member 170. The severed tissue is removed via the aperture 186 in the rotatable member 180 and through the suction nozzle 124 via a conduit (not shown) in the handpiece assembly 121 to the vacuum source 160. It is also contemplated that the cutting element 141 may include any suitable cutting implement and may be vibrated at a high rate of speed (i.e., in an ultrasonic range).

Figure 6:
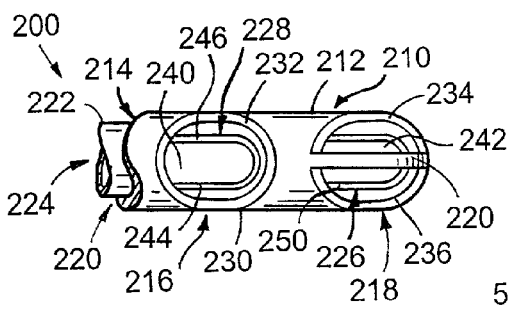
FIG. 6 is a fragmentary view of the distal end of a surgical instrument of the surgical system of FIG. 1.

Referring now to FIGS. 6–10, a number of embodiments of the distal end of the surgical instrument 120 that can be used to remove varicose veins are illustrated. As shown in FIG. 6, the surgical instrument preferably includes an outer stationary member 210 and an inner stationary member 220.

The outer stationary member 220 includes a fitting (not shown) and an elongated member 212.

The elongated member 212 of the outer stationary member 210 preferably includes an aperture 214 extending longitudinally therethrough and two ports or openings 216 and 218. The ports 216 of the elongated member 210 are preferably located at or near the distal end of the elongated member 210 and are arranged in a row along the side of the elongated member 210. The ports 216 and 218 have a generally cylindrical shape and each preferably include a pair of cutting edges 230, 232, 234, and 236. It will be recognized that the ports 216 and 218 can be any size and shape to receive vein tissue. A guard 220 is preferably disposed across the port 218 to limit the amount of vein tissue that can enter into the port 178 to be severed.

The rotatable member 220 preferably includes a base (not shown) and an elongated member 222. The elongated member 222 of the rotatable member 220 preferably includes an aperture 224 extending longitudinally therethrough and two cutting elements 226 and 228. The elongated member 222 of the rotatable member 220 is preferably disposed coaxially within the elongated member 212 of the outer stationary member 210. The elongated member 222 of the rotatable member 220 is preferably fabricated from stainless steel. It is contemplated that the elongated member 222 may be manufactured from any suitable material.

The cutting elements 226 and 228 of the elongated member 222 of the rotatable member 220 are disposed near the distal end of the elongated member 222. The cutting elements 226 and 228 of the rotatable member 220 preferably includes two ports or openings 240 and 242 disposed in the outer surface of the elongated member 222. The ports 240 and 242 have a generally cylindrical shape and each preferably includes a pair of cutting edges 244, 246, 248, and 250. The cutting edges 244, 246, 248, and 250 of the ports 240 and 242 are sharp and cooperate with sharpened edges of the ports 216 and 218 of the outer stationary member 210. It will be recognized that the cutting elements 226 and 228 may be a blade, abrading burr, or an ultrasonic element.

As the rotatable member 220 rotates, the ports 216 and 218 of the rotatable member 220 periodically aligns with the ports 240 and 242, respectively, of the outer stationary member 210 to admit vein tissue. When the vein tissue enters into the ports, the vein tissue is severed or sheared between the cutting edges 244, 246, 248 and 250 of the rotatable member 220 and the cutting edges 230, 232, 234, and 236 of the outer stationary member 210. The severed issue is removed from the surgical site by a vacuum source (not shown).

Figure 7:
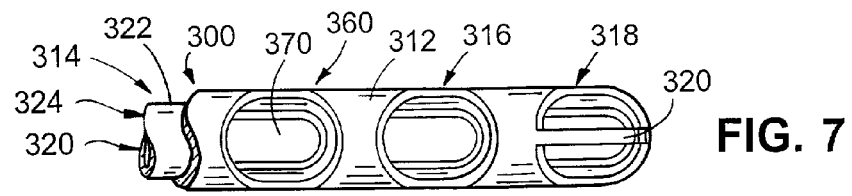
FIG. 7 is a fragmentary view of another embodiment of the distal end of a surgical instrument of the surgical system of FIG. 1.

Referring now to FIG. 7, a distal end of another surgical instrument 300 to remove undesired veins is illustrated which in many respects corresponds in construction and function to the previously described surgical instrument of FIG. 6. Components of the surgical instrument 300 which generally correspond to those components of the surgical instrument 200 of FIG. 6 are designated by like reference numerals in the three-hundred series. As shown in FIG. 7, the surgical instrument 300 includes another port 360 in the outer stationary member 310 and a corresponding port 370 of the rotatable member 320 to sever vein tissue. It will be recognized that the surgical instrument 300 may include any suitable number of ports in the outer stationary member 310 and the rotatable member 320 to cut vein tissue.

Figure 10:
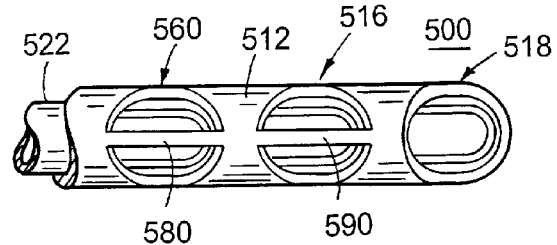
FIG. 10 is a fragmentary view of another embodiment of the distal end of the surgical instrument of the surgical system of FIG. 1.

Referring now to FIG. 10, a distal end of another surgical instrument 500 to remove undesired veins is illustrated which in many respects corresponds in construction and function to the previously described surgical instrument 300 of FIG. 7. Components of the surgical instrument 500 which generally correspond to those components of the surgical instrument 300 of FIG. 5 are designated by like reference numbers in the five-hundred series. As shown in FIG. 10, the surgical instrument 500 includes guards 580 and 590 that extend across ports 560 and 570 of the surgical instrument 500, and the distal port 518 is configured without a guard.

Figure 8:
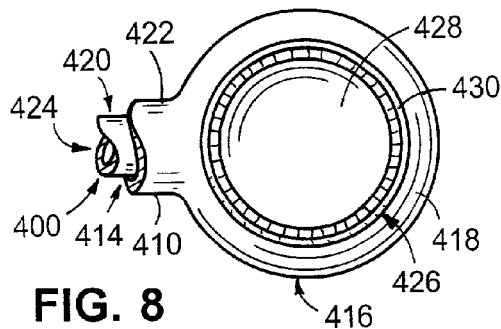
FIG. 8 is another embodiment of a distal end of a surgical instrument of the surgical system of FIG. 1.
Figure 9:
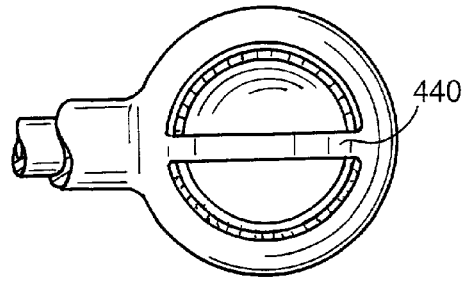
FIG. 9 is a fragmentary view of another embodiment of the distal end of the surgical instrument of the surgical system of FIG. 1.

Referring now to FIG. 8, a distal end of another the 20 surgical instrument 400 is illustrated. The surgical instrument 400 preferably includes an outer stationary member 410 and a rotatable member 420. The outer stationary member 410 includes a fitting (not shown) and an elongated member 412.

The elongated member 412 of the outer stationary member 410 preferably includes an aperture 414 extending longitudinally therethrough and opening or port 416. The port 416 of the elongated member 412 is preferably located at or near the distal end of the elongated member 412. The port 416 has a generally round shape and preferably includes a cutting edge 418. It will be recognized that the port 416 can be any size and shape to receive vein tissue. A guard 440 (see FIG. 9) may be disposed across the port 416 to limit the amount of vein tissue that can enter into the port 416 to be severed.

The rotatable member 420 preferably includes a base (not shown) and an elongated member 422. The elongated member 422 of the rotatable member 420 preferably includes an aperture 424 extending longitudinally therethrough and a cutting element 426. The elongated member 422 of the rotatable member 420 is preferably disposed coaxially within the elongated member 412 of the outer stationary member 410. The elongated member 412 is preferably fabricated from stainless steel. It is contemplated that the elongated member 412 may be manufactured from any suitable material.

The cutting element 426 of the elongated member 422 is disposed at or near the distal end of the elongated member 422. The cutting element 426 preferably includes a port or opening 428 disposed in the outer surface of the elongated member 422. The port 428 has a generally substantially round shape and a cutting edge 430 disposed around the periphery of the port 428. The cutting edge 430 of the port 428 is sharp and cooperates with the sharpened edge of the port 416 of the outer stationary member 410. It will be recognized that the cutting element 426 may comprise a blade, abrading burr, or ultrasonic element.

As the rotatable member 420 rotates, the port 428 of the rotatable member 420 periodically aligns with the port 416 of the outer stationary member 410 to admit vein tissue. When the vein tissue enters into the port, the vein tissue is severed or sheared between the cutting edge 430 of the rotatable member 420 and the cutting edge 418 of the outer stationary member 410. The severed tissue is removed from the surgical site by a vacuum source (not shown).

Figures 11, 12:
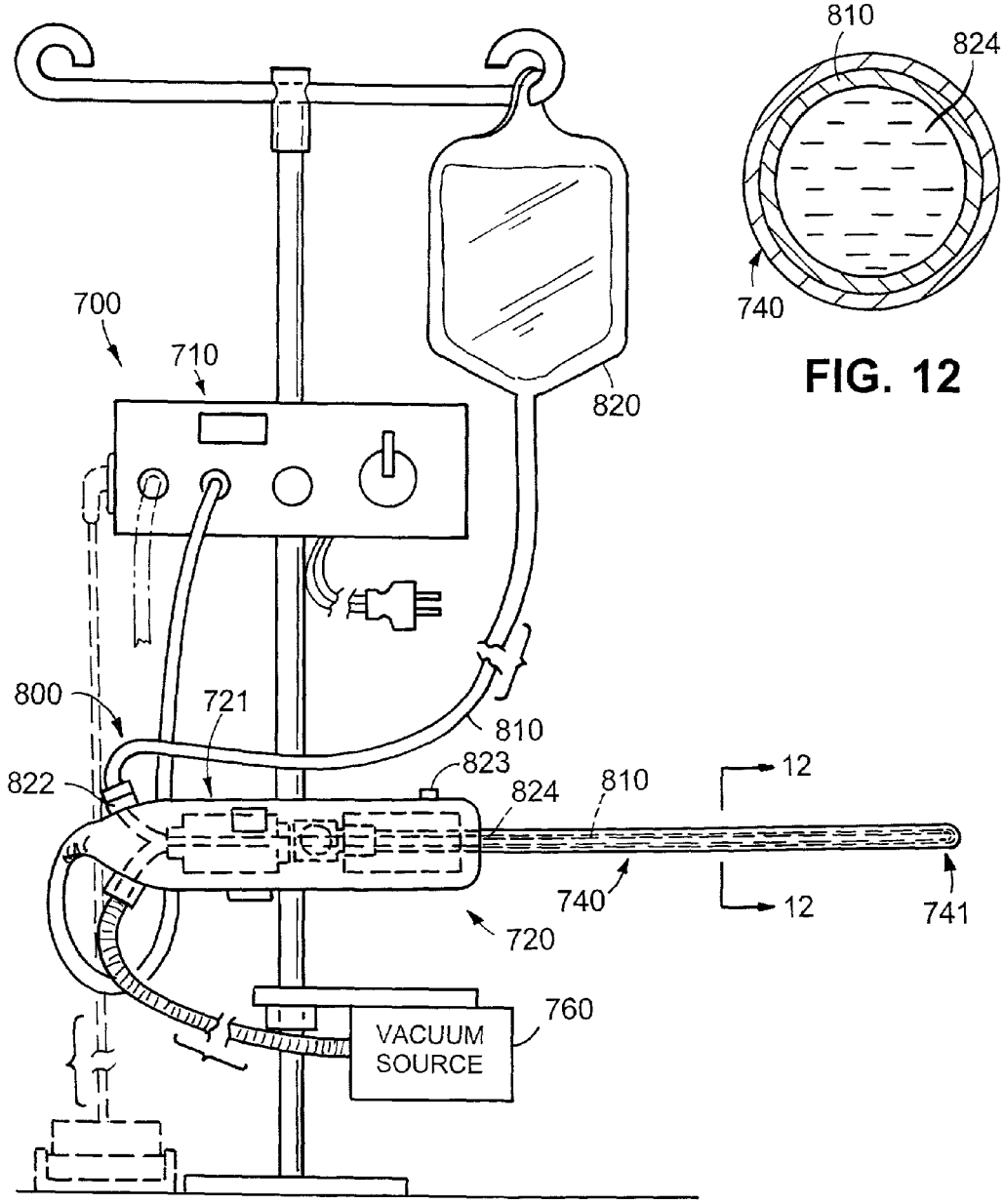
FIG. 11 is a side elevational view of another embodiment of a surgical system to remove undesired veins in a venous system of a patient.
FIG. 12 is a cross-sectional view taken about line 12 of FIG. 11.

Referring now to FIG. 11, another surgical system 700 is illustrated which in many respects corresponds in construction and function to the previously described surgical system 100 of FIG. 1. Components of the surgical system 700 which generally correspond to those components of the surgical instrument 100 are designated by like reference numbers in the seven-hundred series.

As shown in FIGS. 11 and 12, the surgical system 700 includes an irrigation assembly 800 that allows saline or other materials to be introduced into the surgical site of the patient. The irrigation assembly 800 preferably includes an elongated member 810 and a saline bag 820. The elongated member 810 has an aperture extending therethrough to allow the saline to flow from the saline bag 820 through the elongated member 810 and into the handpiece assembly via a coupling member 822 when a trigger member 823 is depressed. The saline flows through a conduit 824 and into the surgical site. It is also contemplated that the coupling member 822 can be located at the distal end of the handpiece assembly or near the proximal end of the elongated member. It will be recognized that the tip of the instrument can be dipped into saline to introduce the saline into the surgical site or the saline can flow through a gap formed between the outer surface of the rotatable member and the inner surface of the outer stationary member. The saline can be suctioned from the surgical site when the vacuum source is activated.

Figure 4:
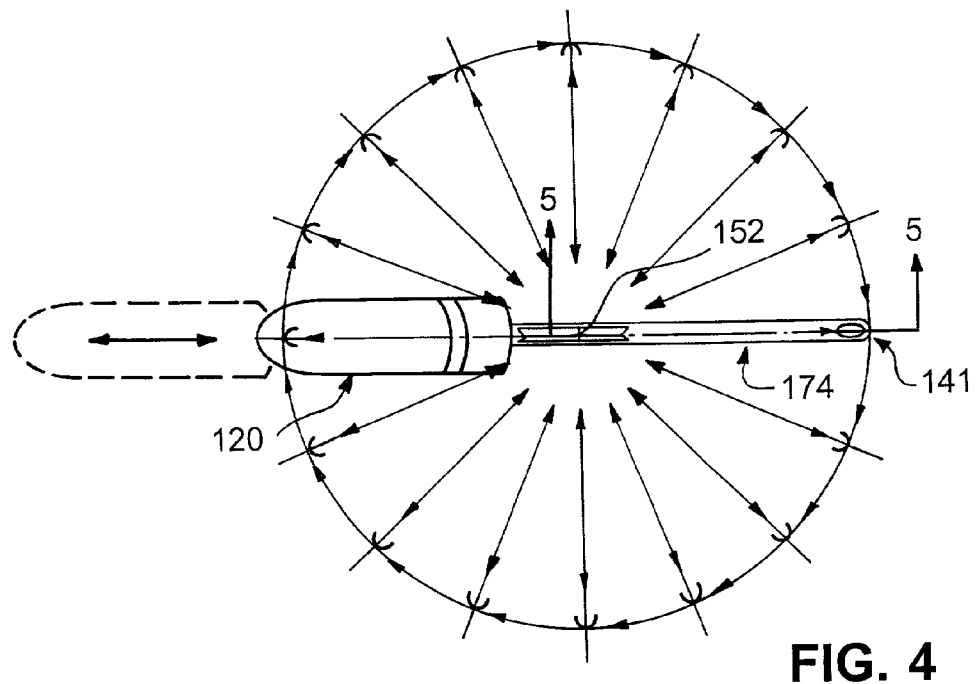
FIG. 4 shows a pattern of movement of the surgical instrument of the surgical system of FIG. 3 to remove undesired veins.

Referring now to FIGS. 3–5, the operation of the surgical system to remove undesired veins, such as, varicose and spider veins, of legs of a patient will be described. Initially, a lower extremity venous doppler is taken of the patient to reveal the incompetent valves of the veins between the superficial vein system and the deeper vein system. If there is incompetence in the greater saphenous veins going into the femoral veins and the lesser saphenous veins going into the popliteal veins, the greater saphenous veins will be ligated and divided. During this procedure, the patient may undergo a general anesthetic, regional anesthetic (i.e., spinal or epidural), or a local anesthetic.

To disconnect the saphenous vein, an incision is made in the groin area to ligate the saphenous vein at its juncture with the femoral vein. All branches of the saphenous vein are ligated and divided with titanium clips and the main greater saphenous vein is ligated proximally and distally. Alternatively, the saphenous vein can be disconnected from the deep veins at a lower point along the leg, such as behind the knee at the lesser saphenous-popliteal junction. This alternative technique may be advisable in circumstances in which treatment of various veins is only necessary in the lower leg.

When the saphenous vein is disconnected from the femoral vein, the blood from the deep veins will be prevented from flowing backing into the saphenous vein, eliminating the primary cause of the varicose veins. While blood can still enter the saphenous vein through the numerous tributary veins, the subsequent permanent closure of the saphenous vein will effectively prevent this occurrence. Once the saphenous vein is disconnected from the femoral vein, the varicose and/or spider veins can be treated. It will also be recognized that the saphenous vein may not have to be disconnected.

To remove the undesired veins, the patient is placed in a trendelenburg position, i.e., feet up, and the incision site is prepared. After proper preparation of the incision site, a surgeon makes a small incision 152 through the skin layer and subcutaneous tissue of the patient. The incision is approximately 2–3 mm and only needs to be large enough to permit the distal end of the surgical instrument 120 to pass therethrough. The incision 152 may be made by a blade, such as a small surgical scalpel, such as a Number 67 scalpel blade. The incision 152 is preferably made near the center of the undesired veins to reach the most veins. It should be apparent that the selection of the incision 152 is for exemplary purposes only and the incision may be made at any suitable location.

After completing the incision 152, the distal end of the surgical instrument 120 is inserted through the incision 152 made at the skin with the motor 122 of the handpiece assembly 121. It is also contemplated that the distal end of the surgical instrument 120 may have a sharp point that enables it to be inserted through the skin layer without having to first make an incision. For example, the surgical instrument 120 may have a retractable scalpel blade.

Once the distal end of the surgical instrument 120 is passed through the incision, the surgeon then activates the switch 128 to cause vacuum suction. The distal end of the surgical instrument 120 is placed on the undesired vein in order to move the vein away from the skin and to remove as much vein tissue with the vacuum suction. The distal end of the surgical instrument 120 is then guided underneath or on the side of the vein to be removed. The surgeon then activates the switch 126 to actuate the cutting element 141 of the surgical instrument 120 at a predetermined speed.

The surgeon can control rotational speed and direction (either unidirectional or oscillatory) using the switch 126 on the handpiece assembly 121 or the foot switch 136. The cutting element 141 can rotate over a wide range of speeds, for example, approximately 500–2000 rpm, and preferably in the range of 800–1200 rpm. Oscillation can be in the ultrasonic range. Saline can also be introduced into the surgical site.

The vacuum suction 160 draws the vein tissue to be cut into the port 178 of the outer stationary member 170. As the vein is drawn into the port 178, the vein is severed by the cutting element 141 of the rotary member 180 and cut into small particles.

As shown in FIG. 4, the surgeon can move the surgical instrument 120 back and forth under the skin and pushing it in and out in a fan-like or circular fashion as permitted to progressively cut away the vein. The amount of cutting varies with the speed of the rotatable member 180, the amount of pressure applied by the surgeon, the sharpness of the cutting edges, and the number and size of the ports on the outer stationary member 170.

After the vein is removed, the incision is closed by conventional techniques, such as, with steri-strips. While suturing of the incision is also possible, it is considered unnecessary due to the small size of the incision, and is also undesirable since suturing the skin can cause scarring. This procedure can then be repeated at another location.

Once the undesired veins are removed, a stocking can be rolled up on the patient's leg and a convatec duoderm elastaplast type stocking can be placed from just proximal to the toes to the upper thigh in order for compression to take place.

The apparatus and methods of the present invention allow various veins to be removed with minimal scarring and without hospitalization. Moreover, the procedure can be performed on an outpatient basis without any of the usual complications of conventional surgical procedures. The procedure can be performed in a short period of time to avoid physician fatigue, minimize anesthesia time for the patient, and increase the number of procedures possible with a given operating room facility.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all respects only as illustrative and not restrictive, and the scope of the invention is, therefore, indicated by the appended claims rather than the foregoing description. All changes that come within the meaning and range of equivalency of the claims are to be embraced within their scope.

An additional embodiment of a surgical instrument for removing veins is shown in FIG. 13. Referring to FIGS. 13 and 13A, surgical instrument 900 includes a housing 901 with an outer stationary member 902 having a proximal hub 904 for attaching member 902 to a handpiece (not shown), and an inner member 906 rotatably received within outer member 902. Inner member 906 includes a proximal hub 908 driven by a motor (not shown).

Outer member 902 has a cylindrical wall 910 defining a lumen 912 in which inner member 906 is received. Inner member 906 defines a lumen 920 through which cut tissue is aspirated, as described above. Hub 904 of outer member 902 includes an irrigation/tumescence inlet connector 914 communicating with a port 916 which extends through outer member wall 910 permitting access of irrigation/tumescence fluid to a channel 918 defined between outer member 902 and inner member 906.

Distal end 922 of outer member 902 includes a window 924 providing access to a cutter 926 located at a distal end 928 of inner member 906. Window 924 is preferably a full radius window with smooth cutting edges (such as is formed on the Smith & Nephew 4.5 mm Full Radius Resector, part no. 3443), and cutter 926 is preferably an incisor blade with serrated cutting edges (such as that formed on the Smith & nephew 4.5 mm Incisor, part no. 3810). This blade combination advantageously produces a surgical instrument for cutting veins which is more aggressive than a standard full radius blade (which has smooth cutting edges on the inner and outer members) but less aggressive than an incisor blade (the inner and outer members of which both have serrated cutting edges).

Hub 904 includes a handpiece attachment element 930 and a locator tab 932 for attaching hub 904 to a handpiece, as described in U.S. Ser. No. 08/630,537, entitled SURGICAL INSTRUMENT HANDPIECE AND SYSTEM, Incorporated by reference herein. Referring to FIG. 1, the trigger mechanism 126 on the handpiece for controlling the rotation of inner member 906 is aligned with window 924 such that trigger mechanism 126 is easily accessible to the surgeon during use of surgical instrument 900 (cutting window 924 generally faces the surgeon during use, as described below). Vacuum switch 128 can be used to turn off the suction for aspiration of cut tissue such that irrigation channel 918 can be used to deliver tumescence fluid to the surgical site.

While surgical instrument 900 is shown having constant diameter inner and outer members 902, 906, the members can be enlarged at all but there distal ends to reduce potential clogging of cut tissue in lumen 920 with their diameters sloping to smaller diameter distal ends. Window 924 can be elongated to provide a larger tissue entry port.

Referring to FIG. 14, a light source, e.g., fiberoptic illuminating device 950, is provided to aid in visualizing a vein during the cutting procedure. The light source is positioned subcutaneously and in close proximity to the vein to be cut, e.g., about 1 to 2 cm from the vein, with light directed at the vein from below or from the side of the vein causing the vein to be shadowed. This enables the surgeon to see the vein through the patient's skin, greatly improving the accuracy, efficacy, and efficiency of the procedure, and enabling the surgeon to see even small, branching veins which can also be advantageously removed using surgical instrument 900.

Illuminating device 950 includes a housing 951 having a handle 952 and an elongated member 954 terminating in a tip 956. Housing 951 contains a fiberoptic bundle 958. Handle 952 includes a lightpost 960 for connecting fiberoptic bundle 958 to a light transmitter (not shown). Lightpost 960 is positioned at proximal end 962 of handle 952 substantially in the direction of a longitudinal axis, A, of illuminating device 950 such that lightpost 960 does not contact the patient during use, which would potentially interfere with the placement of illuminator tip 956 within the patient, and does not interfere with the surgeons grip on handle 952.

Member 954 has a small outer diameter of, e.g., only about 0.165", to minimize tissue trauma. Tip 956 of illuminating device 950 or the distal end of fiberoptic bundle 958 (or both) is oriented at an oblique angle, θ, to the longitudinal axis, A. As a result, light emitted from device 950 is directed at an angle to axis, A, in the range of about 30–85°, preferably about 70°. Member 954 has a length, L1, of about 7.5", such that a large vascular region can be accessed from a single skin portal, and handle 952 has a length, L2, of about 3.75". Member 954 and handle 952 are preferably made from stainless steel.

Referring also to FIG. 14A, handle 952 is somewhat hourglass shaped for ease of handling by the surgeon. Handle 952 has, e.g., a thickness, T1, at waist section 964 of about 0.375", and a larger thickness, T2, of about 0.5" nearer to its upper and lower ends. Sides 966, 968 of handle 952 include grooves 970 to facilitate grasping of handle 952 by the surgeon.

Figure 15:
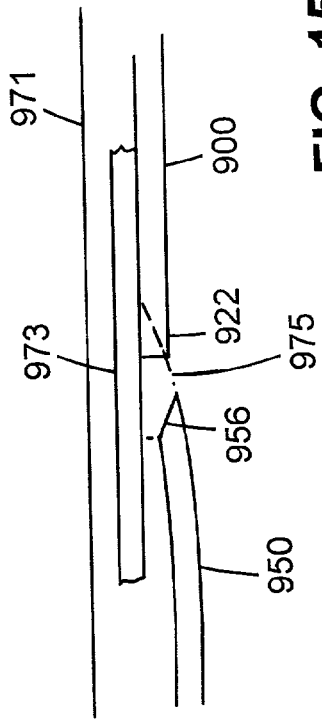
FIG. 15 illustrates the placement of the fiberoptic transilluminator beneath a patient's skin.

Referring to FIG. 15, in use, the surgeon uses an ink marker to outline on the patient's skin 971 the veins to be removed. The surgeon places illuminating device 950 through a first incision in the patient's skin to a location in proximity of a vein 973 to be removed, with the light from illuminating device 950 directed generally upwardly or to the side of the vein to shadow the vein. When placed beneath the vein, illuminating device 950 directs a light cone 975 upward so the surgeon can see the vein shadowed through the skin. Alternatively, the vein can also be shadowed and seen through the skin when the cone of light is directed at the vein from the side of the vein.

Once the vein is in view, the surgeon makes a second incision in the patient's skin spaced by a few inches from the first incision with the vein to be removed located between the incisions. The surgeon then places cutting instrument 900 through the second incision and locates distal end 922 of cutting instrument 900 underneath the vein and facing tip 956 of illuminating device 950. The surgeon then activates cutting instrument 900 to cut the vein.

Illuminating device 950 permits the surgeon to visualize the vein and the distal end 922 of the cutting instrument 900 through the patient's skin during cutting. Illuminating device 950 also aids the surgeon in identifying other diseased vessels, particularly small branches of veins which are otherwise difficult to see.

Tumescence is preferably carried out prior to cutting to shrink the vessels thus limiting blood loss and improving illumination. After cutting is completed, further tumescence can limit blood flow and speed healing. Irrigation is preferably carried out during cutting. Tumescence and irrigation fluid can be delivered through surgical instrument 900, through the illuminating device, as described below, or through both instruments.

Referring to FIG. 16, an alternative fiberoptic illuminating device 950a includes a fiberoptic bundle 958 as shown in FIG. 14, and a separate fluid channel 972. Fluid channel 972 is preferably a straight channel having an internal diameter of about 1 mm. Handle 952a includes a connector 974 for attaching an input fluid line (not shown) to handle 952a to supply fluid to a proximal end 982 of fluid channel 972, and a valve 976 for controlling flow of irrigation and tumescence fluid. The curvature in fiberoptic bundle 958 leading to lightpost 960 facilitates the placement of both lightpost 960 and connector 974 at the proximal end 962 of handle 952a.

Connector 974 has, e.g, either or both of a luer fitting 978 and a tapered hose barb 980. Valve 976 is spring loaded to be biased in an off position, and can be pushed for intermittent supply of fluid or locked on for continuous fluid supply. Channel 972 has an open distal end 982a, and can include distal side openings (not shown) to provide an alternative flow profile of irrigation and tumescence fluid. Member 954a has a small outer diameter of, e.g., only about 0.165", to minimize tissue trauma.

Figure 17:
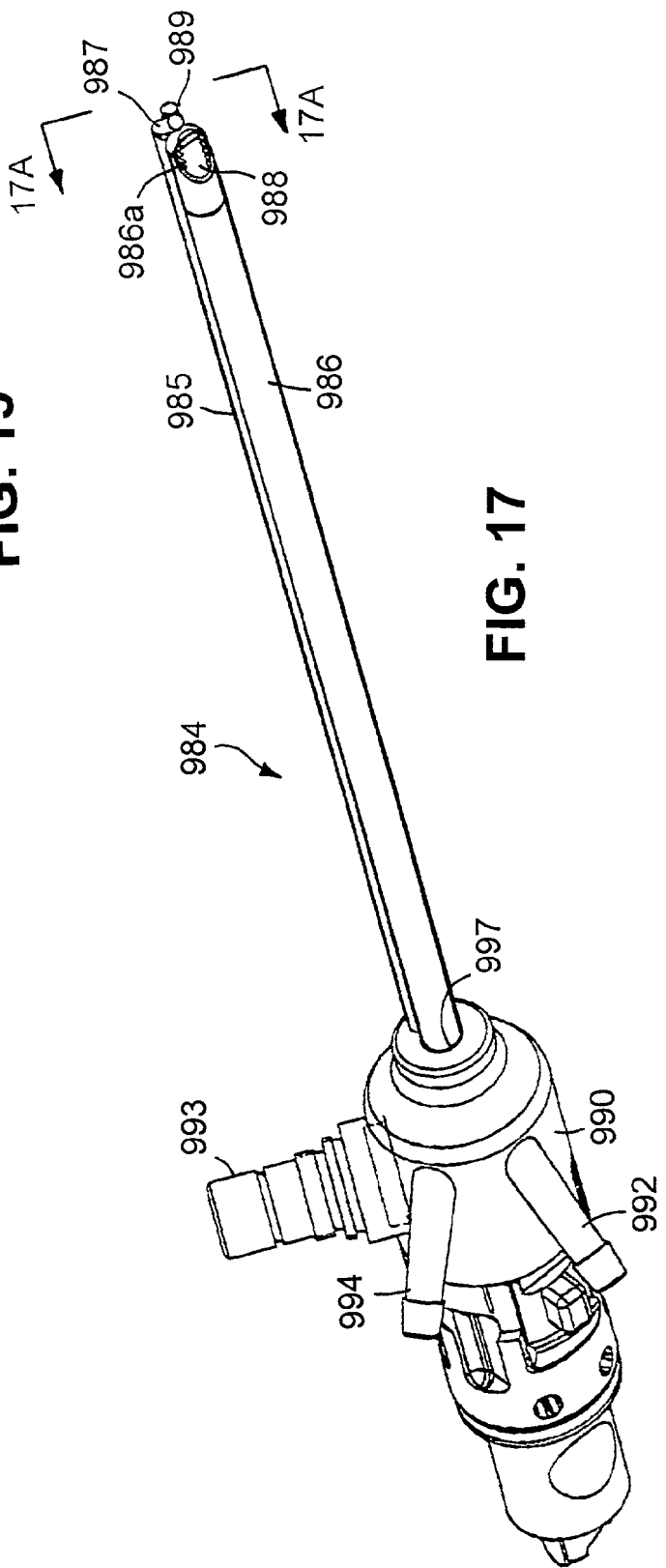
FIG. 17 shows an additional embodiment of a surgical instrument for removing undesired veins.
Figure 17A:
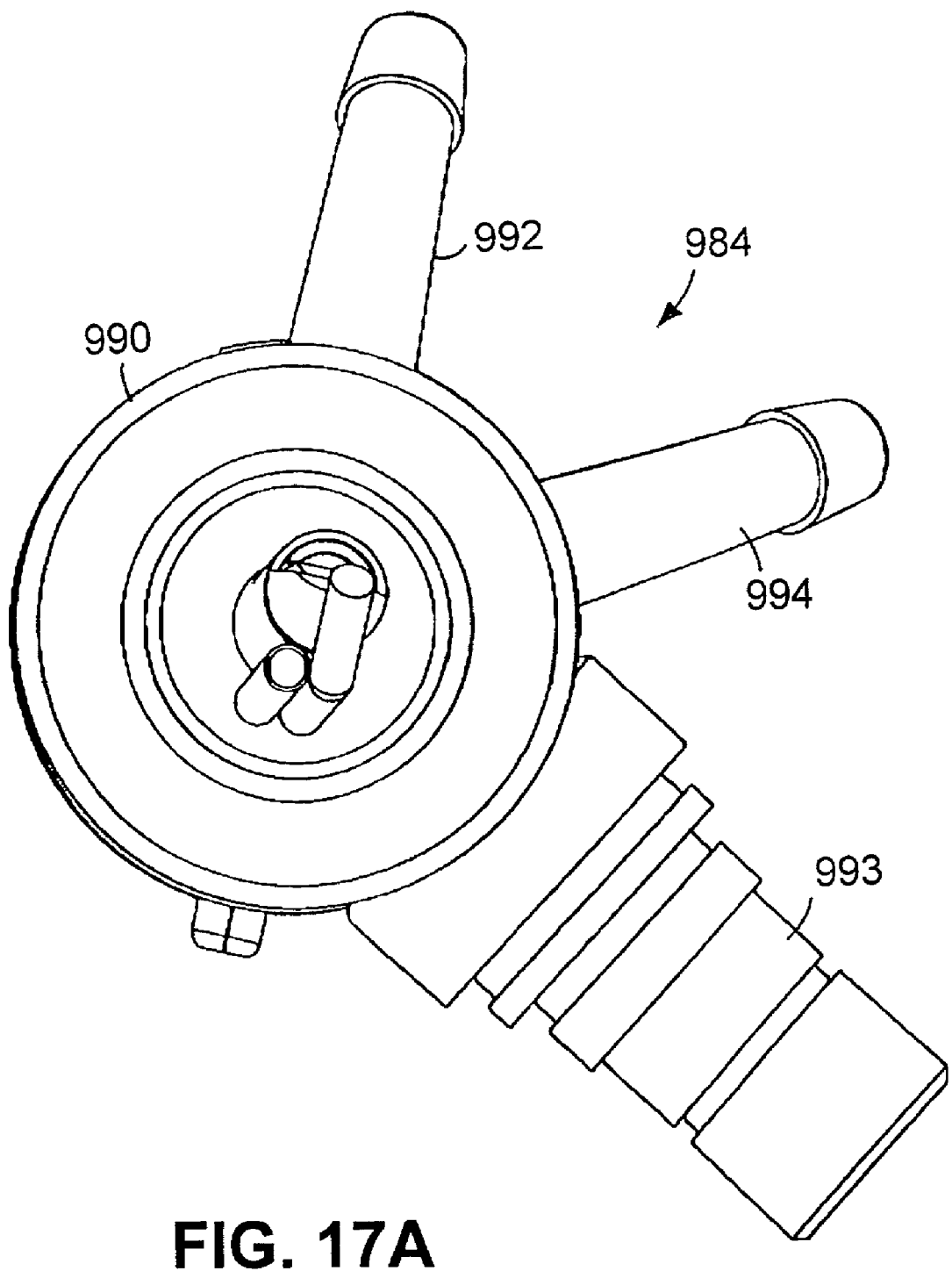
FIG. 17A is an end view of the surgical instrument of FIG. 17, taken along lines 17A—17A.

Referring to FIGS. 17 and 17A, an integral surgical illuminating device 984 includes an outer cutting member 986, an inner cutting member 986a, and a fiberoptic bundle 985 attached to the external surface of outer cutting member 986. A distal tip 987 of fiberoptic bundle 985 is set at an angle relative to the longitudinal axis of device 984 of, e.g., about 0 to 90°, preferably about 45 to 70°, and positioned adjacent to the outer member window 988 to direct the light at a vein positioned above or beside outer member window 988. In the embodiment shown, surgical instrument 984 also includes a separate line 989 attached to the external surface of outer member 986 and distally directed along the longitudinal axis of instrument 984 for delivering fluid to the surgical site. Tine 989 can replace fluid supply channel 918 defined between the inner and outer members (described above), or line 989 can be in addition to fluid channel 918. Alternatively, surgical instrument 984 need not include line 989 and both tumescence and irrigation are conducted through channel 918.

Attached to proximal end 997 of outer member 986 is a hub 990 having a connector 992 for introduction of fluid to line 989, a lightpost 993 for attaching fiberoptic bundle 985 to a light source (not shown), and a connector 994 for introduction of fluid to channel 918 (described above). Surgical instrument 984 is otherwise as described above with reference to FIG. 14.

Other applications for the use of illuminating devices 950, 950a, and 984 include lipoma (fatty tumor removal) and liposuction. During these procedures, the illuminating device can provide visualization of the veins in the area of surgery to aid the surgeon in avoiding the veins.

Other embodiments are within the scope of the following claims.

What is claimed is:

1. A device for illuminating a body structure, consisting of:
   a housing having a distal portion configured for subcutaneous insertion into a patient's tissue and positioning in proximity of the body structure, and a proximal portion having a proximally facing surface having two connectors extending therefrom,
   a light path supported by the housing and configured for directing light at the body structure, wherein one of the connectors connects to the light path, and
   a fluid line supported by the housing, wherein the other of the connectors connects to the fluid line.

2. The device of claim 1 wherein the light path connector extends substantially in the direction of a longitudinal axis of the housing.

3. The device of claim 1 wherein the housing includes a generally hour glassed-shape handle in cross-section.

4. The device of claim 1 wherein the light path comprises a fiberoptic.

5. The device of claim 4 wherein the fiberoptic comprises a fiberoptic bundle.

6. The device of claim 1 wherein a distal end of the light path is oriented at an oblique angle to a longitudinal axis of the housing.

7. The device of claim 1 wherein the distal portion of the housing is oriented at an oblique angle to a longitudinal axis of the housing.

8. The device of claim 1 wherein a distal end of the light path and the distal portion of the housing are oriented at an oblique angle to a longitudinal axis of the housing.

9. The device of claim 1 wherein the fluid line is substantially straight.

10. The device of claim 1 wherein the light path is curved.

* * * * *